United States Patent [19]
You et al.

[11] Patent Number: 5,418,459
[45] Date of Patent: May 23, 1995

[54] METHOD AND APPARATUS FOR FLAW DETECTION USING AN AC SATURATING FIELD GENERATED BY A FIRST COIL AND AN EDDY CURRENT SENSOR SECOND COIL

[75] Inventors: Zhongqing You, Port Chester; Robert A. Brooks, White Plains; Paul J. Bebick, Bronx, all of N.Y.

[73] Assignee: Magnetic Analysis Corporation, Mt. Vernon, N.Y.

[21] Appl. No.: 134,097

[22] Filed: Oct. 8, 1993

[51] Int. Cl.6 ............... G01N 27/90; G01N 27/82
[52] U.S. Cl. ................... 324/240; 324/237; 324/220; 324/238
[58] Field of Search ............... 324/228, 236, 237, 240, 324/238, 242, 221, 229, 232, 234, 239, 243, 225, 220

[56] References Cited
U.S. PATENT DOCUMENTS

| | | | |
|---|---|---|---|
| 3,562,635 | 2/1971 | Parker | 324/212 |
| 3,852,663 | 12/1974 | Brooks et al. | 324/233 |
| 3,875,502 | 4/1975 | Neumaier | 324/242 |
| 3,900,783 | 8/1975 | Mansson | 324/233 |
| 4,188,577 | 2/1980 | Mhatre et al. | 324/220 |
| 4,461,995 | 7/1984 | Harris | 324/240 |
| 4,644,272 | 2/1987 | Janos | 324/240 |
| 4,808,926 | 2/1989 | Graham et al. | 324/240 |
| 5,117,182 | 5/1992 | Cecco et al. | 324/242 |
| 5,311,127 | 5/1994 | Bisiaux | 324/242 |

Primary Examiner—Sandra L. O'Shea
Assistant Examiner—Roger Phillips
Attorney, Agent, or Firm—Robin, Blecker, Daley & Driscoll

[57] ABSTRACT

A method for nondestructive examination of an object of type having localized permeability variations therein and varying surface conditions and grain structures comprises the steps of AC flux saturating a localized surface area of the object so as to magnetically saturate the surface area to quiet localized permeability variations therein and to set up a stabilized high level primary field on the surface substantially unalterable by the varying surface conditions and grain structures in the object and detecting eddy currents in the surface area. Coil structure and apparatus for implementing the method are also defined. Further, the method is disclosed as being implemented in part by the use of components of a pre-existing object evaluation device.

27 Claims, 5 Drawing Sheets

METHOD AND APPARATUS FOR FLAW DETECTION USING AN AC SATURATING FIELD GENERATED BY A FIRST COIL AND AN EDDY CURRENT SENSOR SECOND COIL

FIELD OF THE INVENTION

This invention relates generally to nondestructive testing of metal objects for flaws therein and pertains more particularly to the detection of flaws existing in hot rolled bar or tubular products.

BACKGROUND OF THE INVENTION

The so-called "eddy current method" for object examination has been in widespread use for many years and involves the generation of eddy currents in an object under testing and determination of defects therein on the basis of detection of such eddy currents and their characteristics.

Eddy current evaluation of magnetic materials is dominantly affected by permeability variations in the object. In various test instances, permeability inhomogeneity of the object gives rise to a sufficiently high noise level to so lessen the "signal-to-noise ratio" as to undermine the efficacy of the testing. The art has, however, long recognized a solution to this problem for encircling coil inspection evaluations, namely, to DC (direct current) magnetically saturate the object such that the detection apparatus sees only a constant or unit permeability.

Situations arise, however, where DC magnetic saturation of the test object is not practical, for example, in the spinning probe inspection of large-diameter steel bar material and thick-walled pipes. In those instances, eddy current testing can be successfully practiced without DC magnetic saturation of the object. However, work surface finishes therein become a problematic factor. Thus, unevenness or surface roughness can give rise to noise generation of greater adverse consequence to signal-to-noise ratio than permeability inhomogeneity.

The art has likewise addressed the surface roughness problem. The eddy current results encompass flaw signals indicative of a defect in the object and noise signals arising from surface roughness. The solution, although of limited applicability, involves selection of an inspection frequency that allows for phase discrimination, i.e., the operator selects a test frequency which maximizes the polar phase difference between the flaw signals and the noise signals so as to increase the signal-to-noise ratio. Cold rolled materials generally have better surface finishes than hot rolled materials and the phase discrimination practice is more beneficial in application to the former materials. In the case of hot rolled materials, the degree of surface roughness can generate excessive polar noise, such that many smaller-depth defects cannot be detected at any phase relationship.

Difficulty accordingly attends eddy current examination of hot rolled materials. If they are nonmagnetic, the DC saturation practice is not applicable and if surface roughness is excessive, eddy current testing is limited. Where the hot rolled material is magnetic, but saturation is not practical as for spinning probe inspection, the same ineffectiveness of eddy current practice is at hand if surface roughness is excessive. In summary, the spinning probe eddy current practice as presently known is seen as usable effectively in examining magnetic hot rolled materials that do not have excessive surface roughness.

AC flux leakage, another inspection method, was introduced a few years ago primarily for testing hot rolled steel materials. The basic principle for AC flux leakage also relies on the skin effect and similarly magnetizes the surface region of the material in order to be able to generate leakage flux in the presence of a defect. Additionally, the magnetization force has to be applied normal to a defect in order to create a leakage flux and subsequently detect the defect.

Examples of the AC flux leakage method, particularly in its application to hot rolled materials, are seen, for example, in U.S. Pat. Nos. 5,023,550 and 4,297,636. The former patent particularly notes the inefficacy of the eddy current method for examination of hot rolled materials and looks to examination thereof by the AC flux leakage method.

SUMMARY OF THE INVENTION

The present invention has as its primary object the provision of an improved method for nondestructive testing for flaws in metallic bar or tubular products, whether magnetic or nonmagnetic.

A more particular object of the invention is to provide an effective method for examining hot rolled objects, i.e., without the above-noted limitations common to heretofore-known methods.

In attaining these and other objects, the invention provides a method for nondestructive examination of an object of type having localized permeability variations therein and varying surface conditions and grain structures, the method comprising the steps of:

(a) disposing a first coil in registry with a surface area of a metallic object to be examined for defects;
(b) driving the primary coil with an excitation signal selected in its characteristics
   (1) to magnetically saturate the surface area under examination to quiet localized permeability variations therein, and
   (2) to set up a stabilized high level primary field on the surface substantially unalterable by the varying surface conditions and grain structures in the object; and
(c) disposing a second coil in registry with the surface area and therewith detecting resulting eddy currents in the surface area.

The primary coil is selected to have a core having a conductivity that avoids eddy current core losses. The secondary coil is selected to have a core having saturation flux density sufficiently high that the secondary coil core is not saturated by the high fringe level of the primary field.

More broadly, the invention provides a method for nondestructive examination of an object of type having localized permeability variations therein and varying surface conditions and grain structures, the method comprising the steps of AC magnetically saturating a broad surface area of the object to quiet localized permeability variations within. It sets up a stabilized high level primary field on the surface substantially unalterable by the varying surface conditions and grain structures in the object, whereby secondary pickup coils detect localized eddy current responses in localized surface areas.

Specifically, the invention involves what applicants denominate as a "high power eddy current" (HPEC) method which is found particularly effective in performing surface testing for very small levels of defects in hot rolled materials.

A conventional eddy current system can have either separate low power primary excitation and secondary pickup coils or only a single coil to perform the function of both primary and pickup coils. A commonly used configuration has two coils, acting as a differential or null pair, which both deliver the primary excitation and sense the response signals, respectively.

The subject HPEC method, however, uses a high power primary coil for the excitation and separate null secondary coils for signal detection.

The "high power" here refers to the high level of sinusoidal or continuous pulse excitation provided to the primary coil, as contrasted with conventional eddy current practices. The main functions of this high power excitation, particularly when testing hot rolled materials, are (1) to magnetically saturate the surface area under inspection to quiet localized permeability variations and (2) to set up a stabilized high level primary field on the surface which cannot be easily altered by the varying surface conditions and grain structures encountered. This is achieved because of the resulting skin effect at the higher excitation frequencies which restricts the resulting magnetic field and the associated eddy current penetration to the surface region. The secondary null sensing coils, on the other hand, detect the very small eddy current disturbances caused by very small localized defects that it crosses within the quieted AC saturated area.

While invention contemplates that apparatus in accordance therewith is self-standing, i.e., is inclusive of all system components, it otherwise looks to apparatus which derives its magnetic field from associated, pre-existing apparatus. Thus, in a further embodiment discussed also below, the magnetic field is derived from such associated apparatus as an induction welder, annealer or hardener.

The foregoing and other objects and features of the invention will be further understood from the following detailed discussion of preferred practices and embodiments thereof and from the drawings wherein like reference numerals identify like components and part throughout.

DETAILED DESCRIPTION OF PREFERRED EMBODIMENTS AND PRACTICES

Figure 1:
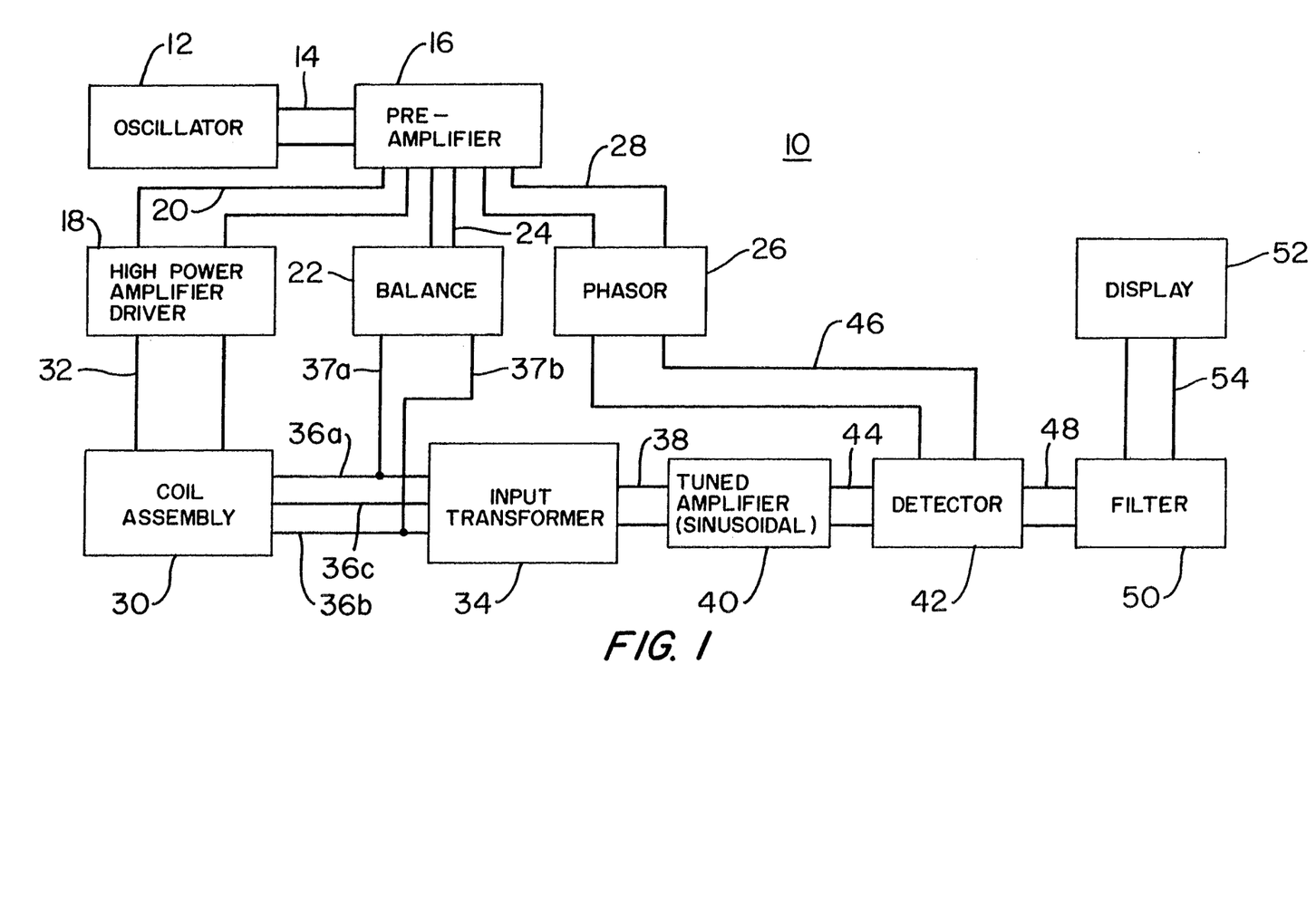
FIG. 1 is a functional block diagram of a self-standing system for implementation of the method of the invention.

Referring to FIG. 1, system 10 of the invention includes signal generator or oscillator 12 which provides an input sinusoidal signal over lines 14 to preamplifier 16. Preamplifier 16 supplies an output to high power amplifier driver 18 over lines 20, a second output to balance circuitry 22 over lines 24 and a third output to phasor circuitry 26 over lines 28. Power amplifier 18 drives the primary of coil assembly 30 over lines 32.

Input transformer 34 has its input lines 36a–c connected to the secondary of coil assembly 30. As discussed below with reference to FIG. 2, the secondary of the coil assembly includes a pair of coils, differentially connected, with the common junction of the coils connected to line 36c and the free coil ends connected respectively to lines 36a and 36b. Balance circuitry 22 output lines 37a and 37b are connected to lines 36a and 36b. As is customary, balance circuitry 22 completes a Wheatstone bridge with the secondary coils and is adjustable to provide a null secondary coil output in set-up of the system prior to its use.

Transformer 34 supplies its output over lines 38 to tuned amplifier (sinusoidal) 40, the output of which is supplied as a first input to detector circuitry 42 over lines 44. Given its sinusoidal nature, amplifier 40 is responsive whether the test excitation is sinusoidal or of continuous pulse type. Phasor circuitry 26 output lines 46 provide a second input to detector circuitry 42. The detector circuitry output is supplied over lines 48 to filter 50, the output of which is applied to display unit 52 over lines 54. The output of filter 50 is also furnished over lines 53 to output threshold trigger circuit 51, which is both amplitude and phase sensitive. Circuit 51 controls alarm & marker/sorter control outputs 49 over lines 47.

With the exception of power amplifier driver 18 and the level of excitation and structure of coil assembly 30, the FIG. 1 system is a conventional version of a phase-sensitive eddy current detection system and incorporating reference is made to commonly-assigned U.S. Pat. Nos. 3,900,793 and 3,852,663 for discussion of the known eddy current testing system.

The known eddy current system coil drive, provided by oscillator 12 and preamplifier 16 is used as the input to power amplifier driver 18 over lines 20. Since this signal is from the same source as the detection reference signal on lines 28, signal detection is automatically synchronized and thus any non-synchronous beating phenomenon is eliminated. The known system also provides the signal amplification, filtering and coil balancing as set forth in FIG. 1. X & Y quadrature output signals are provided by detector circuitry 42 and filter 50 increases the signal-to-noise ratio. Displaying is desirably in both linear and polar forms.

The power level of primary coil excitation, per the subject invention, is typically about two kilowatts, but may be any value above approximately one kilowatt, as contrasted with approximately ten watts in the known eddy current testing system. The highly increased power level is selected particularly, as above noted (1) to magnetically saturate the surface area under inspection to quiet localized permeability variations and (2) to set up a stabilized high level primary field on the surface which cannot be easily altered by the varying surface conditions and grain structures encountered. This is achieved because of the resulting skin effect at the higher excitation frequencies employed, which restricts the resulting magnetic field and the associated eddy current penetration to the surface region. Per the invention, the excitation frequency may be any value above approximately five kilohertz and is typically eight to ten kilohertz.

Figure 2:
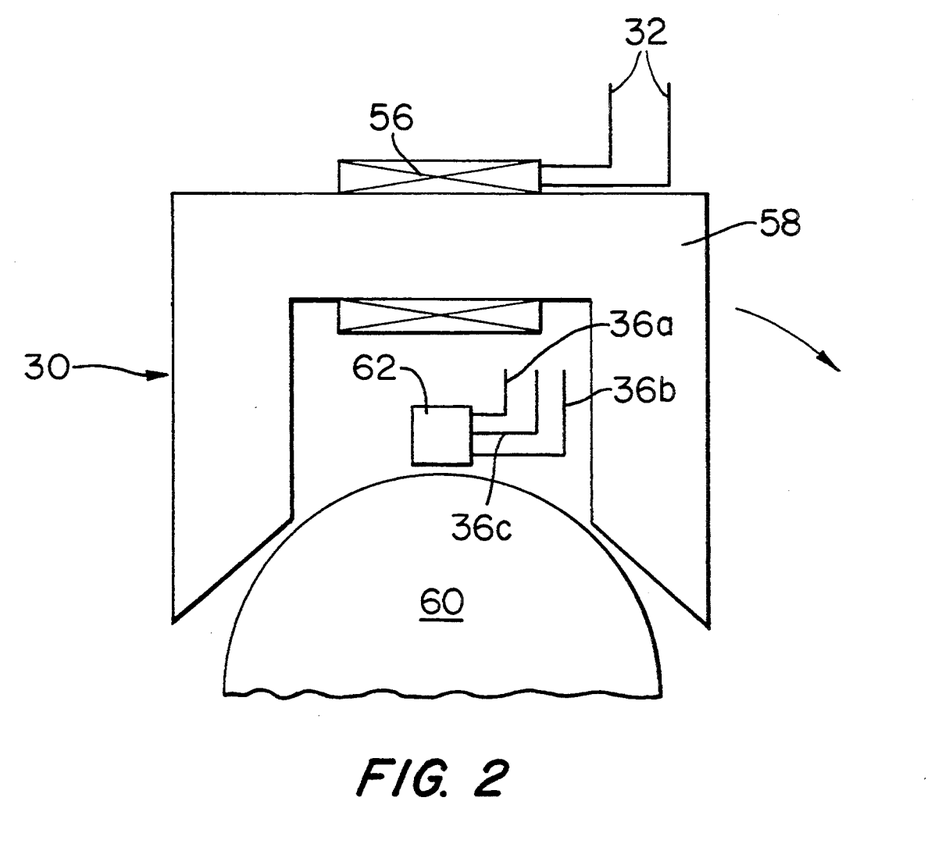
FIG. 2 is a diagram descriptive of a first embodiment of a coil assembly in accordance with the invention for use in the FIG. 1 system.

Referring to FIG. 2, coil assembly 30 includes primary coil 56 which is applied centrally about the upper course of core 58, the legs of which extend into proximity with specimen 60 being examined. The assembly is constructed as a reasonably small yoke assembly to increase its magnetic efficiency. A very low conductivity core is chosen to avoid high eddy current core losses, which would attend the high power and high frequency required. This is a very important consideration because the heating generated by the eddy current and hysteresis losses can be excessive and destructive.

A series resonance circuit may be incorporated to increase the drive efficiency. The series resonance circuit of course would correspond in its resonant frequency to the selected drive frequency.

Secondary coil unit 62 is supported centrally of core 58 also in proximity with specimen 60. As is seen in FIG. 3, secondary coil unit 62 includes two coils 64 and 66, connected in opposition to one another and wound about cores discussed below.

Figure 3:
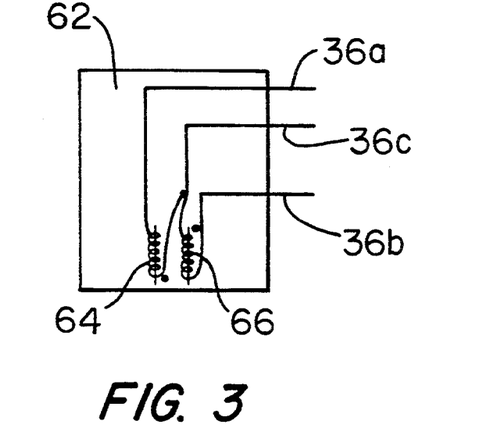
FIG. 3 is an enlarged showing of the secondary coil unit 62 of FIG. 2.

Coil assembly 30 has a counterpart coil assembly of the same construction as that depicted in FIGS. 2 and 3 displaced one-hundred and eighty degrees apart and both coil assemblies are supported to rotate about the specimen being tested, whereby longitudinal specimen defects are detectable.

As respects the pick-up (secondary) coil unit 62, it is to be noted that an air-cored coil may not be able to satisfy the sensitivity requirements for very small defects. On the other hand, a low saturation magnetic core can be saturated and rendered insensitive too easily, since the magnetic fringe field around it is very strong. Therefore, tiny cores having very high saturation flux density that is difficult to saturate are used along with a differential null coil probe pair.

The HPEC system both creates and detects changes in eddy currents via their changing field disturbances due to the presence of very small level material defects. In addition, the method of the invention can be applied to and can successfully inspect nonmagnetic conducting materials, whereas competing leakage flux systems cannot. Furthermore, a HPEC system has less restriction on the direction of the applied primary field than that of the magnetization force used in the leakage flux method. Due to the orthogonal relationship between the applied primary magnetic field and the induced eddy current field, per the invention, an anomaly such as a crack can disturb either the magnetic field or the induced eddy current field, or both, depending on its orientation. Accordingly, the HPEC method can always sense the defect anomaly for a given primary field direction as long as the secondary coils are correctly oriented, whereas for the leakage flux method, the magnetization field has to be applied across the crack.

Figure 4:
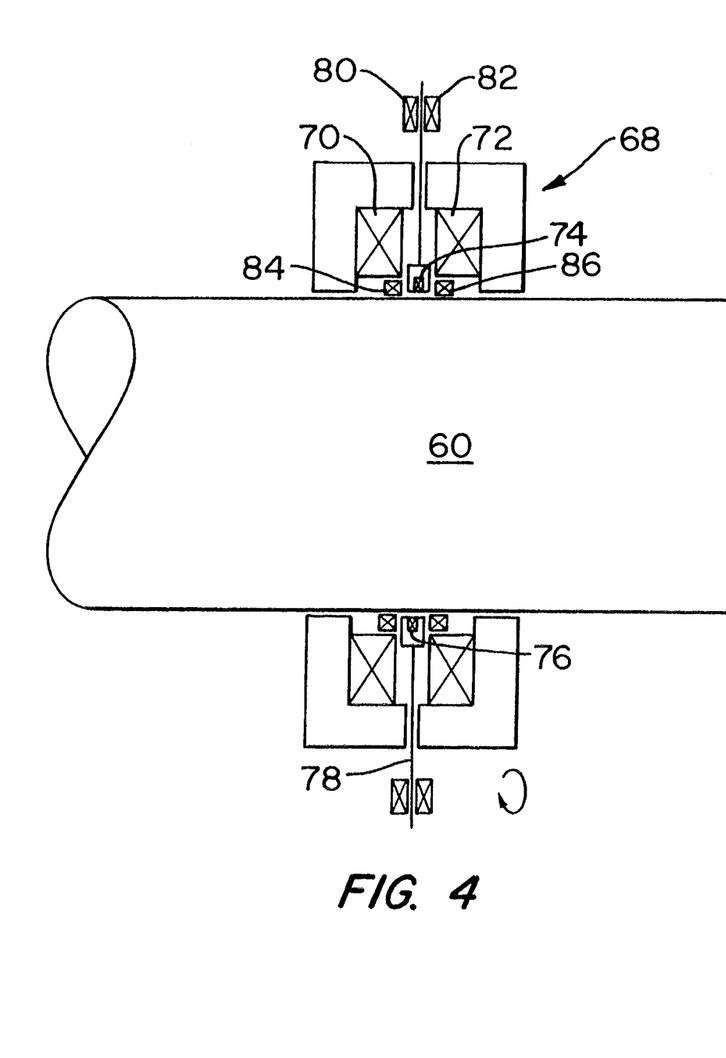
FIG. 4 is a diagram descriptive of a second embodiment of a coil assembly in accordance with the invention for use in the FIG. 1 system.
Figure 5:
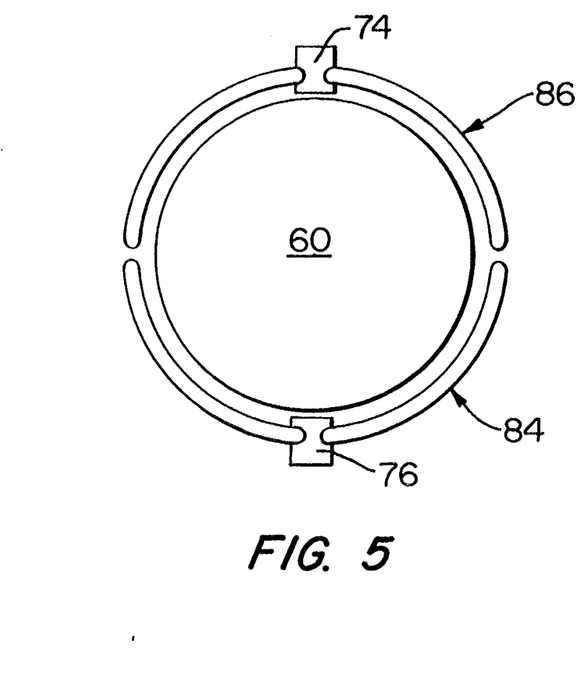
FIG. 5 is a partial right side elevation of the FIG. 4 showing.

An alternate HPEC arrangement and practice is shown in FIGS. 4 and 5. Here, core 68 is longitudinally split and has primary coils 70 and 72 nested in the split core parts. This assembly is fixedly disposed in circumscribing relation to specimen 60 being examined. A central pair of rotating secondary null coils 74 and 76 are disposed one-hundred and eighty degrees apart and are radially adjustable in slides (not shown) on a rotating disk 78 for smaller diameter products, to detect longitudinally oriented defects. Pole piece inserts would supplement core 68 for the smaller diameter products.

Slip ring and brush assemblies 80 and 82 are provided for the respective rotating secondary null coils.

Separate, fixedly disposed, encircling null coils 84 and 86 are provided under the primary coils and can be used to detect holes and transversely oriented defects as the product is longitudinally driven through the rotating probes/encircling coils arrangement. Coils 84 and 86 are segmented as seen in FIG. 5 into separate detectors or may be multiplexed into a single detector to increase individual sensitivity and signal-to-noise ratio. Each rotating probe requires its own detection system as do the encircling null coils, all synchronized to the primary coil's driving oscillator reference/system clock. Different sized coils 84 and 86 would be used for smaller diameter products.

In this embodiment, the power level of primary coil excitation is increased above the high level for the first embodiment, since the full periphery of the object being evaluated is to be magnetically saturated. The excitation power level here is thus at two kilowatts and above. The frequency is the same as for the first embodiment.

Figure 6:
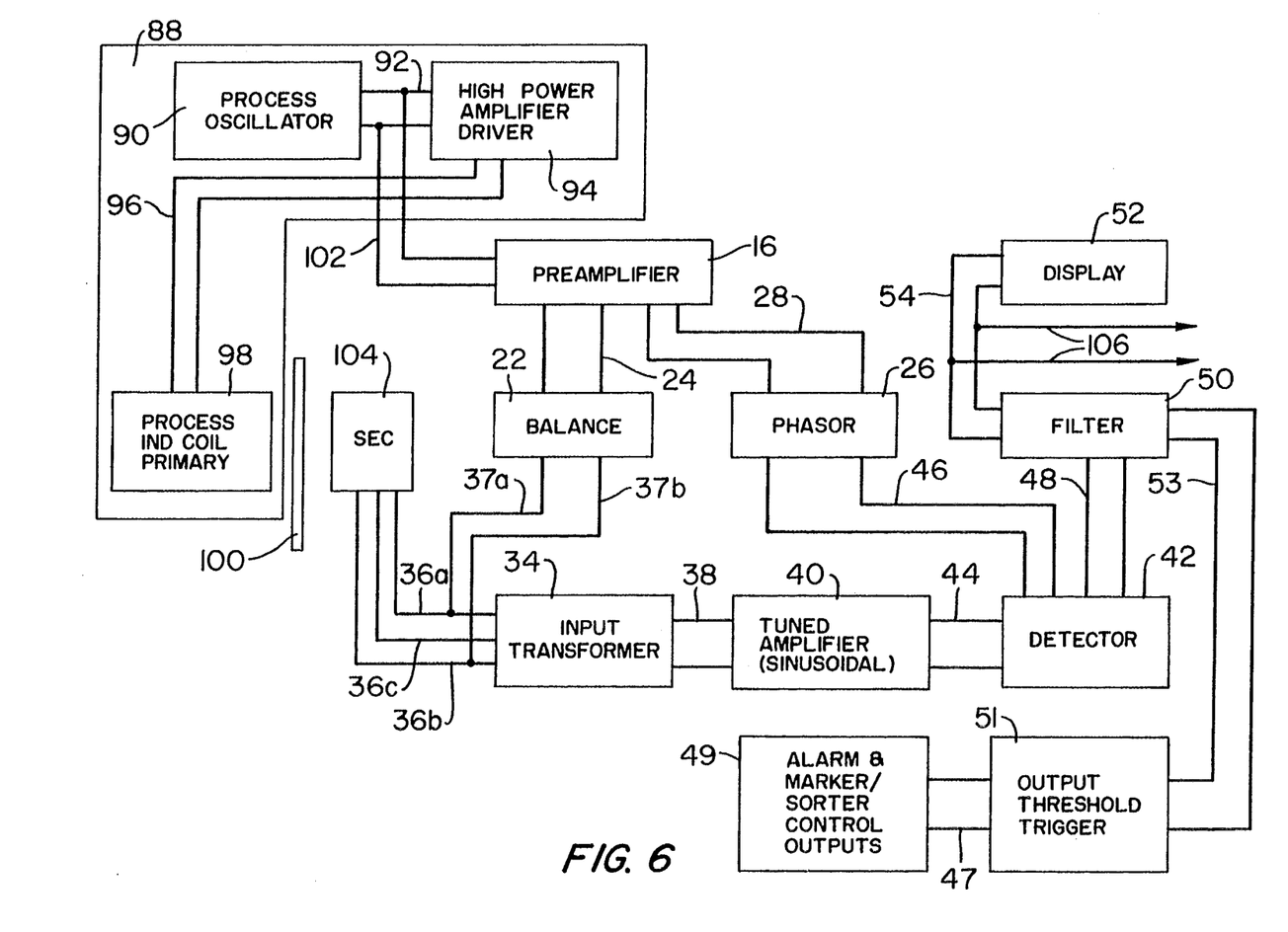
FIGS. 6 and 7 comprise a functional block diagram of a system for implementation of the method of the invention wherein the magnetic field is derived from associated, pre-existing apparatus.
Figure 7:
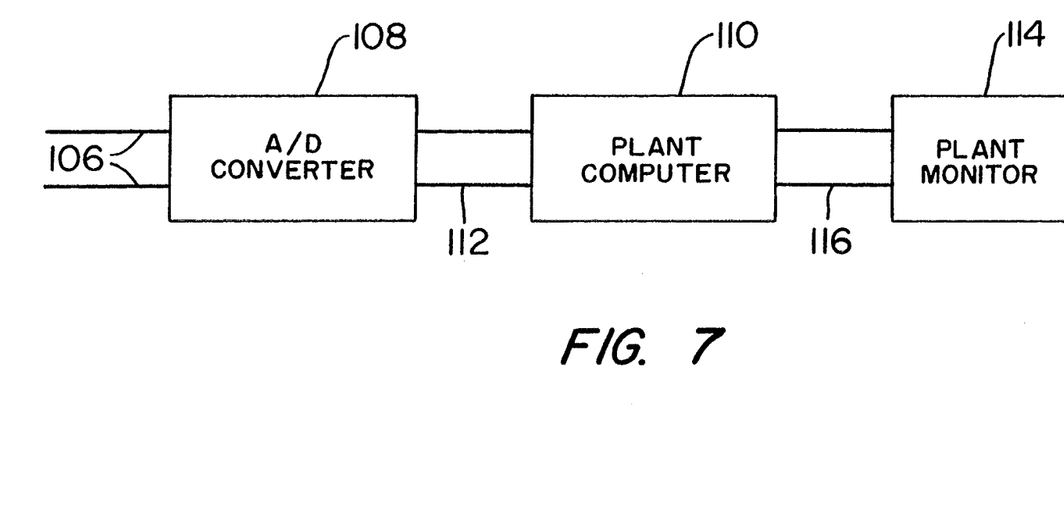

While the first and second embodiments involve self-standing or self-contained apparatus, the embodiment of FIGS. 6 and 7 now discussed relies on associated apparatus for establishing the magnetic field. Induction welders, annealers and hardeners and the like thus contain components suited for so supplementing the invention.

Turning to FIGS. 6 and 7, component 88 is of the associated apparatus, pre-existing device and includes process oscillator 90, the output of which is directed over lines 92 to high power amplifier driver 94, which is again of either sinusoidal or continuous pulse variety. The amplifier driver output is applied over lines 96 to the high power induction coil 98 (PROCESS IND COIL PRIMARY), which is likewise a component of the associated apparatus and serves as the magnetic field generator for specimen 100, providing high power induction and product eddy current related fields.

The output of oscillator 90 is furnished over lines 102 to preamplifier 16, which with like numbered components of FIG. 6 corresponding to FIG. 1 call out the system components used with the associated apparatus.

One system component differs, namely, the secondary coil (SEC) 104 includes only the secondary coil of coil assembly 30 of FIG. 1. This component is secondary coil unit 62 of FIG. 3, suitably encased to adapt to the high temperature environment of the associated apparatus.

The system implements, to this juncture, flaw detection in specimen 100. It has the further aspect of providing for instantaneous on-line process evaluation and, to that end, has the further components of FIG. 7, which are fed the output of filter 50 over lines 106. The filter output includes data in analog form indicative of such parameters as flaws, hardness, case depth, weld pool condition, thermal profiles, and the like. The analog signals are fed over lines 106 to analog-to-digital converter 108 and the resulting digital signals are conveyed to plant computer 110 over lines 112. This unit typically contains data analysis programs and the results of analysis and other information are furnished as signals to plant monitor 114 over lines 116, by which an operator can take corrective action to normalize the process at hand. As desired, the corrective action may be implemented by automated apparatus, i.e., providing an unattended closed loop for control of the process.

Various changes to the particularly disclosed methods and coil assemblies may evidently be introduced without departing from the invention. Accordingly, it is to be appreciated that the particularly discussed and depicted preferred embodiments and practices of the invention are intended in an illustrative and not in a limiting sense. The true spirit and scope of the invention are set forth in the ensuing claims.

What is claimed is:

1. A method for nondestructive examination of an object of type having localized permeability variations therein and varying surface conditions and grain structures, said method comprising the steps of:
    (a) disposing a primary coil in registry with a surface area of an object to be examined for defects;
    (b) driving said primary coil with a sinusoidal excitation signal selected in its characteristics
        (1) to AC flux saturate the surface area under examination to quiet localized permeability variations therein, and
        (2) to set up a stabilized high level primary field at said surface substantially unalterable by said varying surface conditions and grain structures in said object and inducing eddy currents therein; and
    (c) disposing a second coil in registry with said surface area and therewith detecting in synchronism with said excitation signal eddy currents in said surface area.

2. The method claimed in claim 1 wherein said primary coil is selected to have a core having a conductivity avoiding eddy current core losses in said core.

3. The method claimed in claim 1 wherein said secondary coil is selected to have cores having saturation flux density sufficiently high that the secondary coil cores are not saturated by said high level primary field.

4. The method claimed in claim 2 wherein said secondary coil is selected to have cores having saturation flux density sufficiently high that the secondary coil cores are not saturated by said high level primary field.

5. The method claimed in claim 1 wherein said primary coil excitation signal has a power level of at least one kilowatt.

6. The method claimed in claim 1 wherein said primary coil excitation signal has a frequency of at least five kilohertz.

7. The method claimed in claim 5 wherein said primary coil excitation signal has a frequency of at least five kilohertz.

8. The method claimed in claim 1 wherein said steps (a) and (b) are practiced by using components of a pre-existing object evaluation device.

9. A method for nondestructive examination of an object of type having localized permeability variations therein and varying surface conditions and grain structures, said method comprising the steps of:
    (a) AC flux saturating a localized surface area of said object by use of a sinusoidal excitation signal so as to magnetically saturate the surface area to quiet localized permeability variations therein and to set up a stabilized high level primary field at said surface substantially unalterable by said varying surface conditions and grain structures in said object and inducing eddy currents therein; and
    (b) detecting in synchronism with said excitation signal eddy currents in said surface area.

10. The method claimed in claim 9 wherein said step (a) is practiced by using an AC signal having a power level of at least one kilowatt.

11. The method claimed in claim 9 wherein said step (a) is practiced by using an AC signal having a frequency of at least five kilohertz.

12. The method claimed in claim 10 wherein said step (a) is practiced by using an AC signal having a frequency of at least five kilohertz.

13. The method claimed in claim 9 wherein said step (a) is practiced by using components of a pre-existing object evaluation device.

14. Apparatus for nondestructive examination of an object of type having localized permeability variations therein and varying surface conditions and grain structures, comprising:
    (a) a primary coil for registry with a surface area of the object to be examined for defects;
    (b) drive means for providing said primary coil with a sinusoidal excitation signal selected in its characteristics
        (1) to AC flux saturate the surface area under examination to quiet localized permeability variations therein, and
        (2) to set up a stabilized high level primary field at said surface substantially unalterable by said varying surface conditions and grain structures in said object and inducing eddy currents therein;
    (c) a secondary coil for registry with said surface area and for detecting eddy currents in said surface area; and
    (d) processing means for processing said detected eddy currents in synchronism with said excitation signal.

15. The apparatus claimed in claim 14 wherein said primary coil has a core having a conductivity avoiding eddy current core losses in said core.

16. The apparatus claimed in claim 14 wherein said secondary coil has cores having saturation flux density sufficiently high that the secondary coil cores are not saturated by said high level primary field.

17. The apparatus claimed in claim 15 wherein said secondary coil has cores having saturation flux density sufficiently high that the secondary coil cores are not saturated by said high level primary field.

18. The apparatus claimed in claim 14 wherein said drive means provides said primary coil excitation signal at a power level of at least one kilowatt.

19. The apparatus claimed in claim 14 wherein said drive means provides said primary coil excitation signal at a frequency of at least five kilohertz.

20. The apparatus claimed in claim 18 wherein said drive means provides said primary coil excitation signal at a frequency of at least five kilohertz.

21. The apparatus claimed in claim 14 wherein said primary coil and said secondary coil are jointly rotatable relative to said object.

22. The apparatus claimed in claim 14 wherein said primary coil is fixedly disposed and is configured to circumscribe said object and wherein said secondary coil is rotatable relative to said object.

23. The apparatus claimed in claim 22 further including a further secondary coil for additional eddy current detection, said further secondary coil being fixedly disposed and configured to circumscribe said object.

24. The apparatus claimed in claim 23, wherein said further secondary coil has plural segments jointly providing said circumscribing of said object.

25. The apparatus claimed in claim 22 wherein said drive means provides said primary coil excitation signal at a power level of at least two kilowatts.

26. The apparatus claimed in claim 22 wherein said drive means provides said primary coil excitation signal at a frequency of at least five kilohertz.

27. The apparatus claimed in claim 12, wherein said primary coil and said drive means are components of a pre-existing object evaluation device.

* * * * *